US008790926B2

(12) United States Patent
Miller

(10) Patent No.: US 8,790,926 B2
(45) Date of Patent: Jul. 29, 2014

(54) TISSUE ENGINEERING SUPPORTS AND METHODS THEREFOR

(75) Inventor: Seth Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 71 days.

(21) Appl. No.: 13/260,021

(22) PCT Filed: Feb. 16, 2011

(86) PCT No.: PCT/US2011/025042
§ 371 (c)(1),
(2), (4) Date: Sep. 23, 2011

(87) PCT Pub. No.: WO2012/112151
PCT Pub. Date: Aug. 23, 2012

(65) Prior Publication Data
US 2012/0208276 A1    Aug. 16, 2012

(51) Int. Cl.
*C12M 3/00* (2006.01)
(52) U.S. Cl.
USPC .......................... 435/397; 435/395; 435/402
(58) Field of Classification Search
CPC ........... C12N 2535/00; C12N 2533/30; C12N 2533/00; C12N 5/0068; C12M 25/14; C12M 3/00
See application file for complete search history.

(56) References Cited

U.S. PATENT DOCUMENTS

| | | | |
|---|---|---|---|
| 5,112,136 A | 5/1992 | Sakuma et al. | |
| 5,284,766 A * | 2/1994 | Okano et al. | 435/397 |
| 6,942,873 B2 * | 9/2005 | Russell et al. | 424/426 |
| 2007/0281353 A1 * | 12/2007 | Vacanti et al. | 435/367 |
| 2008/0044864 A1 * | 2/2008 | Jeong et al. | 435/91.2 |
| 2008/0070282 A1 * | 3/2008 | Hwang et al. | 435/91.2 |
| 2009/0298166 A1 | 12/2009 | Fang et al. | |

FOREIGN PATENT DOCUMENTS

EP        0 382 214        8/1990

OTHER PUBLICATIONS

Desai, Tejal A. "Micro-and nanoscale structures for tissue engineering constructs." Medical Engineering & Physics 22.9 (2000): 595-606.*
Deutsch, Jennifer, et al. "Fabrication of microtextured membranes for cardiac myocyte attachment and orientation." Journal of biomedical materials research 53.3 (2000): 267-275.*
Isenberg, Brett C., and Joyce Y. Wong. "Building structure into engineered tissues." Materials Today 9.12 (2006): 54-60.*
Akiyama, Y. et al., "Ultrathin poly(N-isopropylacrylamide) grafted layer on polystyrene surfaces for cell adhesion/detachment control," Langmuir, 2004, Published on Web May 26, 2004, vol. 20, pp. 5506-5511.
Baroli, B., "Hydrogels for Tissue Engineering and Delivery of Tissue-Inducing Substances," J. Pharm. Sci., Sep. 2007, vol. 96, No. 9, pp. 2197-2223.
Cartmell, S.H. et al., "Mechanical conditioning of bone cells in vitro using magnetic microparticle technology," European Cells and Materials, 2002, vol. 4, Suppl. 2, pp. 130-131.
Gimsa, U. et al., "Actin is not required for nanotubular protrusions of primary astrocytes grown on metal nano-lawn," Molecular Membrane Biology, May-Jun. 2007, vol. 24, No. 3, pp. 243-255.
Hassan, C.M. et al., "Structure and Applications of Poly(vinyl alcohol) Hydrogels Produced by Conventional Crosslinking or by Freezing/Thawing Methods," Advances in Polymer Science, 2000, vol. 153, pp. 38-65.
International Search Report and Written Opinion for PCT/US2011/025042 mailed Mar. 30, 2011.
Isenberg, B.C. et al., "A thermoresponsive, microtextured substrate for cell sheet engineering with defined structural organization," Biomaterials, Jun. 2008, vol. 29, No. 17, pp. 2565-2572.
Kwon, O.H. et al., "Accelerated Cell Sheet Recovery by Co-Grafting of PEG with PIPAAm Onto Porous Cell Culture Membranes," Biomaterials, 2003, vol. 24, pp. 1223-1232.
Lowman, A.M. et al., "Hydrogels," Encyclopedia of Controlled Drug Delivery—vol. 1, 1999, pp. 397-418.
Mason, C., "Tissue Engineering Skin: A Paradigm Shift in Wound Care," Medical Device Technology, Dec. 2005, vol. 16, pp. 32-33.
Matsuda, N. et al., "Tissue Engineering Based on Cell Sheet Technology," Advanced Materials, 2007, vol. 19, pp. 3089-3099.
Tsang, V.L. et al., "Fabrication of Three-Dimensional Tissues," Adv. Biochem. Engin/Biotechnol., 2006, vol. 103, pp. 189-205.
Yamada, N. et al., "Thermo-Responsive Polymeric Surfaces; Control of Attachment and Detachment of Cultured Cells," Makromol. Chem., Rapid Communications, 1990, vol. 11, pp. 571-576.
Yamato, M. et al., "Thermally Responsive Polymer-Grafted Surfaces Facilitate Patterned Cell Seeding and Co-Culture," Biomaterials, 2002, vol. 23, pp. 561-567.

* cited by examiner

*Primary Examiner* — Daniel Sullivan
*Assistant Examiner* — Peter Anthopolos
(74) *Attorney, Agent, or Firm* — Foley & Lardner LLP

(57) ABSTRACT

The present disclosure relates to supports and scaffolds for cell and tissue engineering. The supports disclosed herein are composed of a thermally responsive material, containing pillars, that is coated with an acrylic polymer, thereby imparting an amphipathic matrix foundation. When exposed to a change in temperature, the coated support reacts by facilitating or repelling hydromolecular interactions. Further disclosed herein are methods for making hydrogels that can support tissue growth.

7 Claims, 1 Drawing Sheet

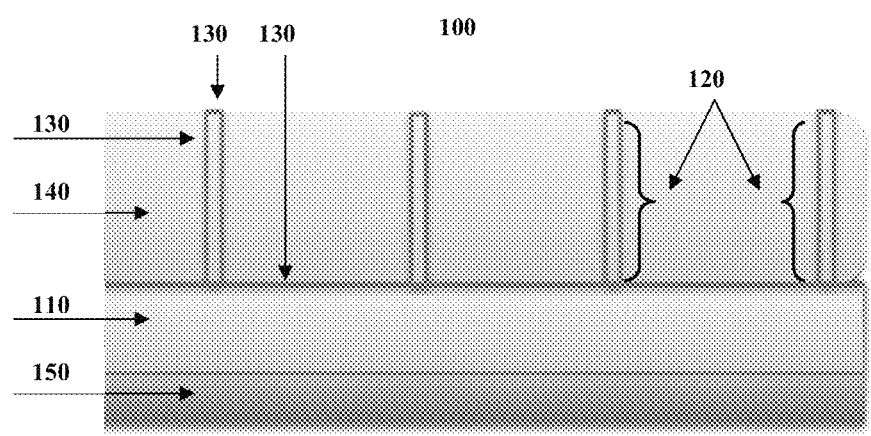

TISSUE ENGINEERING SUPPORTS AND METHODS THEREFOR

CROSS-REFERENCE TO RELATED APPLICATIONS

The present application is a U.S. national stage application of International Application No. PCT/US2011/025042, filed on Feb. 16, 2011, the entire contents of which is incorporated herein by reference in its entirety.

TECHNICAL FIELD

The present disclosure relates generally to apparatuses for tissue engineering. In particular, the present disclosure includes a support mechanism for the production of hydrogel matrices for cell and tissue production.

BACKGROUND

The following description is provided to assist the understanding of the reader. None of the information provided or references cited is admitted to be prior art.

Tissue engineering involves the use of living cells to develop biological substitutes for tissue and organ replacement. In order for tissue engineering to be practical, however, biological matrices must be developed that allow for cell and tissue growth that approximates natural growth. Tissue engineering matrices can be natural or artificial structures, which are capable of facilitating a variety of processes. Such biological structures serve multiple purposes, including, supporting cell or tissue attachment, migration, delivery, and retention. In addition to cells and/or tissues, the matrices can contain drugs, bioactive agents, and/or fluids, e.g., cell growth medium. As such, these structures can be seeded with cells and cultured in vitro or directly implanted into a tissue.

Along these lines, tissue engineering applications require structures composed of varying degrees of size and thickness, which impart the concomitant durability of the matrix and/or tissue. In this regard, the structure and strength of the matrix or tissue can vary and, for applications requiring manipulation, transportation, and/or implantation, a stable tissue-support complex is necessary to ensure the integrity of the tissue. Additionally, non-disruptive mechanisms for severing the tissue-support complex is an important consideration in the development of new strategies for tissue engineering and organ replacement.

SUMMARY

In one aspect, the present disclosure provides a support for tissue engineering that includes a thermoconductive scaffold with one or more pillars and a thermoresponsive polymer coating the one or more pillars, wherein the thermoresponsive polymer is capable of transitioning from a hydrophobic to a hydrophilic state in response to a change in temperature. In one embodiment, the thermoconductive scaffold is made of copper, silver, zinc, magnesium, iron, gold, aluminum, aluminum nitride, aluminum oxide, brass, cobalt, graphite, or beryllium, or any combination thereof. In an illustrative embodiment, the thermoconductive scaffold is made of copper.

In one embodiment, the one or more pillars have a width from about 0.5-5 mm. In one embodiment, the one or more pillars are positioned throughout the thermoconductive scaffold in angled, straight, slanted, tapered, polygonal, rectangular, square, circular, curved, diagonal, random, concentric, patterned, perimetric, polygonal, diamond, hexagonal, or triangular configurations, or any combination thereof. In one embodiment, the thermoresponsive polymer is PIPAAm, which is hydrophobic at temperatures above 32° C. and hydrophilic at 32° C. or below.

In one aspect, the present disclosure provides methods for tissue engineering that include applying a hydrogel solution to a thermoconductive scaffold with one or more pillars, wherein the one or more pillars are coated in a thermoresponsive polymer, and allowing the hydrogel solution to congeal. In one embodiment, the methods further include cooling the thermoconductive scaffold. In one embodiment, the cooling lowers the temperature to at least 32° C. In one embodiment, the cooling is by a Peltier cooler. In one embodiment, the methods further include allowing the hydrogel to release from the thermoconductive scaffold.

In one embodiment, the hydrogel matrix capable of facilitating tissue growth, tissue engineering, cell growth, or cell-sheet growth, or any combination thereof. In one embodiment, the hydrogel matrix is poly(hyaluronic acid), poly (sodium alginate), poly(ethylene glycol), diacrylate, or chitosan, or any combination thereof. In one embodiment, the hydrogel has perforations or indentations or both, following the release from the thermoconductive scaffold. In one embodiment, the methods further include filling the perforations or indentations with the hydrogel solution.

In one embodiment, the methods further include culturing cells on or within the hydrogel to form one or more cell-layers or cell-sheets, or both. In one embodiment, the methods further include harvesting the one or more cell-layers or cell-sheets, or both. In one embodiment, the one or more cell-layers or cell-sheets is a monolayer. In one embodiment, the one or more cell-layers or cell-sheets are stratified layers.

In another aspect, the present disclosure provides a kit for tissue engineering support containing a thermoconductive scaffold with one or more pillars, wherein the one or more pillars are coated in a thermoresponsive polymer. In one embodiment, the kit includes one or more hydrogel components. In one embodiment, the kit includes instructions for making the support.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

FIG. 1 is an illustrative embodiment of a hydrogel-based tissue engineering support complex.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used herein, unless otherwise stated, the singular forms "a," "an," and "the" include plural reference. Thus, for example, a reference to "a tissue" or "the tissue" includes a plurality of tissues.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein, the terms "amphipathic" or "amphiphilic" are meant to refer to any material that is capable of polar and non-polar, or hydrophobic and hydrophilic, interactions. These amphipathic interactions can occur at the same time or in response to an external stimuli at different times. For example, when a specific material, coating a thermoresponsive support, is said to be "amphipathic," it is meant that the coating can be hydrophobic or hydrophilic depending upon external variables, such as, e.g., temperature.

As used herein, the terms "hydrogel" or "gel" or "hydrogel matrix" are used interchangeably, and encompass polymer and non-polymer based hydrogels, including, e.g., poly(hyaluronic acid), poly(sodium alginate), poly(ethylene glycol), diacrylate, chitosan, and poly(vinyl alcohol)-based hydrogels. "Hydrogel" or "gel" is also meant to refer to all other hydrogel compositions disclosed herein, including hydrogels that contain polymers, copolymers, terpolymer, and complexed polymer hydrogels, i.e., hydrogels that contain one, two, three, four or more monomeric or multimeric constituent units. Also used herein, the terms "tissue matrix" or "tissue hydrogel" similarly refer to any composition formed into a porous matrix into which cells or tissue can grow in three dimensions. Hydrogels are typically continuous networks of hydrophilic polymers that absorb water.

As used herein, the term "organ" refers to a part or structure of the body, which is adapted for a special function or functions, and includes, but is not limited to, the skin, the lungs, the liver, the kidneys, and the bowel, including the stomach and intestines. In particular, it is contemplated that organs which are particularly susceptible to dysfunction and failure arising from an injury are amendable to tissue-engineered reconstruction and are encompassed by the term "organ." "Tissues" are singular or multiply-layered structures, i.e., monolayers or stratified layers of cells, which are organ constituents. One or more different tissues may form an organ or organs. An organ may also be composed of only one type of tissue or cell, or different tissues or cells.

As used herein, the term "polymer" refers to a macromolecule made of repeating monomer or multimer units. Polymers of the present disclosure, include, but are not limited to, poly(hyaluronic acid), poly(sodium alginate), poly(ethylene glycol) (PEG), poly(lactic acid) polymers, poly(glycolic acid) polymers, poly(lactide-co-glycolides) (PLGA), poly(urethanes), poly(siloxanes) or silicones, poly(ethylene), poly(vinyl pyrrolidone), poly(-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(methacrylic acid), polylactic acid (PLA), polyglycolic acids (PGA), nylons, polyamides, polyanhydrides, poly(ethylene-co-vinyl alcohol) (EVOH), polycaprolactone, polyvinylhydroxide, poly(ethylene oxide) (PEO), and polyorthoesters or a co-polymer or terpolymer formed from at least two or three members of the groups, respectively.

As used herein, the terms "scaffold' or "substrate" or "support", used in the context of a tissue and/or hydrogel production, refer to any surface or structure capable of supporting hydrogel, or any other matrix, including cells and/or tissues grown therewith. Such supports or substrates have various contemplated surfaces, and/or are composed of materials, which include, but are not limited to, glass, metal, plastic, and/or materials coated with polymers for binding and/or immobilization of a hydrogel scaffold, e.g., poly(N-isopropylacrylamide) (PIPAAm), isopropylacrylamide butyl methacrylate copolymer (IBc), butyl methacrylate (BMA), poly-NIPAAm-co-AAc-co-tBAAm (IAtB), N,N-dimethylaminopropylacrylamide (DMAPAAm), poly(N-acryloylpiperidine)-cysteamine (pAP), PIPAAM-carboxymethyl dextran benzylamide sulfonate/sulfate (PIPAAm-CMDBS), or N,N-methylene-bis-acrylamide cross-linked polymer, PIPAAm-PEG, or any combinations thereof.

As used herein, the terms "thermoconductive material" or "thermoconductive substrate" or "thermoconductive support" refer to a structure that is capable of conducting heat, i.e., retaining or changing in response to external heat or energy. Typical thermoconductive materials include metals, such as, but not limited to, copper, silver, zinc, magnesium, iron, gold, aluminum, aluminum nitride, aluminum oxide, brass, cobalt, beryllium, and graphite, or any combination thereof.

As used herein, the terms "thermoresponsive material" or "thermoresponsive polymer" refer to a compound, material, monomer, polymer, co-polymer, terpolymer, or any combination thereof, that is capable of altering its state or property, i.e., hydrophobicity or hydrophilicity, in response to a change in temperature.

Support Structures for Hydrogel Production and Tissue Engineering

Tissue matrices provide an environment for cells to grow and correspondingly guide the process of tissue formation in three dimensions. Synthetic polymers are attractive matrix materials because they can be readily manufactured with a wide range of reproducible properties and structures. Polymer tissue matrices, depending on their composition, provide varying degrees of mechanical support for withstanding compressive and/or tensile forces. In this regard, maintaining the shape and integrity of the matrix is important for certain tissue engineering applications, such as implanting newly formed tissue or a tissue-matrix complex into a patient. Typical tissue-matrix structures include various types of hydrogels, which differ in their durability.

Hydrogels are three-dimensional, hydrophilic structures composed of homopolymers or co-polymers. These matrices can be employed for a variety of biomedical applications, including, but not limited to, intervertebral disc replacement, disc augmentation, wound care, cartilage replacement, joint replacement, surgical barriers, gastrointestinal devices, drug delivery, cosmetic and reconstructive surgery, such as, e.g., soft tissue and organ reconstruction and/or vascular reconstruction, and breast enlargement. See, e.g., Hassan & Peppas, *Advances in Polymer Science*, Vol. 153, Springer-Verlag Berlin Heidelberg, pp. 37-65 (2000); Lowman et al., Ed., John Wiley and Sons, pp. 397-418 (1999).

The proper design of polymer-based hydrogels allows them to exhibit a vast range of mechanical and biological functions. Synthetic polymeric materials can be precisely controlled in material properties, quality, and mode of manufacture. Moreover, the present disclosure enables the production of synthetic polymers by various techniques, thereby facilitating the consistent supply of such hydrogels in large quantities. The mechanical and physical properties of synthetic polymers can be readily adjusted through variation of molecular structures so as to fulfill their functions without the use of either fillers or additives.

An array of synthetic polymers can be utilized to fabricate hydrogel matrices for cell and tissue production. These materials are typically employed as structural elements in the hydrogel, and include, but are not limited to, poly(hyaluronic acid), poly(sodium alginate), poly(ethylene glycol) (PEG), diacrylate, chitosan, poly(vinyl alcohol) (PVA), poly(glycolic acid) (PGA), poly(lactic acid) (PLA), poly lactic co-lactic acid (PLLA), and poly(lactic acid)-poly(glycolic acid) (PLGA). See Table 2. These polymers are also extensively used in other biomedical applications such as drug delivery and are FDA approved for a variety of applications. A number of PEG, PVA, PGA, PLA, PLLA and PLGA and other synthetic polymer tissue matrices are also known in the art. In one embodiment, the hydrogel matrix is composed of poly(hyaluronic acid), poly(sodium alginate), PEG, diacrylate, chitosan, PVA, PGA, PLA, PLLA, and/or PLGA, or any combination thereof.

These hydrogel polymers provide a native-like biological milieu for developing tissue. Due to their mechanical fragility, however, hydrogels may be difficult to handle in the absence of extreme care. As such, hydrogels can break, fracture, and/or disintegrate when relatively weak stress is applied, for example, when transferring the gel from growth culture to storage or for patient implantation. Accordingly, an advantageous feature of the present disclosure relates to supporting apparatuses for the production, aseptic handling, manipulating, and transportation of intact hydrogels, including cell and/or tissue-embedded hydrogels. These delicate hydrogel matrices are advantageously reinforced when they congeal on and/or proximal to a scaffolding with supporting pillars.

In this respect, the present disclosure provides a support or substrate apparatus for the production and handling of hydrogel scaffolds, while not disrupting the integrity of cells or tissues therein. Hydrogel matrix constructs can be formed on thermoconductive scaffolds or supports containing one or more pillars coated with a thermoresponsive polymer. The scaffold is thermoconductive, i.e., thermally conductive, in that it can conduct, contain, and/or transfer heat for certain periods of time. Thermal conductivity is measured as the quantity of heat that passes through a particular area and thickness of a material when a temperature gradient is present. Thermal conductivity can be measured in watts per meter-kelvin or W/(m·K), which can be quantitatively determined by methods well known in the art. See, e.g., Sakuma et al., Method of and apparatus for measuring thermal conductivity, U.S. Pat. No. 5,112,136. In suitable embodiments, the thermal conductivity of the scaffold and/or pillars is at least about 1, 5, 10, 50, 75, 100, 125, 150, 175, 200, 250, 300, 350, 390, 400, 500, or 1000 W/(m·K). In one embodiment, the thermal conductivity of the scaffold and/or pillars is about 400 W/(m·K).

Metals are typically thermoconductive and can be employed as the thermoconductive materials that include the support structure and/or pillars. In this regard, the support structures and/or pillars may be composed of one or more metals which impart a suitable conductivity. In some embodiments, the thermoconductive support or scaffold is composed of materials that include, but are not limited to, copper, silver, zinc, magnesium, iron, gold, aluminum, aluminum nitride, aluminum oxide, brass, cobalt, graphite, and beryllium, or any other suitable metal or material. In one embodiment, the thermoconductive scaffold is composed of copper. In another embodiment, the thermoconductive scaffold is composed of any material capable of forming a desired scaffold structure, which is subsequently coated with a thermally conductive layer, such as a metal. The metal layer can be applied at an appropriate thickness to allow for suitable scaffold thermal conductivity. In one embodiment, the scaffold is composed of plastic such as, e.g., poly(methyl methacrylate), and then plated with copper to a thickness of about from 0.01 to 1 µm by electroless deposition, followed by electrodeposition to a thickness of about from 1-50 µm.

The thermoconductive scaffold contains one or more pillars protruding from the base of the structure. The pillars allow for increased surface area for cellular attachment, while additionally providing a network of supporting structures to increase the rigidity of complexes formed thereon. In one embodiment, the scaffolds are manufactured as an integrated construct composed of a single structure. In another embodiment, the pillars may be detachably removed. In this regard, the scaffold is manufactured by drilling holes into a base structure, e.g., a copper foundation, and the pillars are subsequently placed into the resulting apertures. In another embodiment, the pillars may be securely affixed to the apertures using, e.g., high-strength glue or adhesive. The pillars function in concert with the entire thermoconductive scaffold, and thus, are likewise, thermoconductive pillars.

In one embodiment, the one or more pillars are composed of a suitable amount of copper, silver, zinc, magnesium, iron, gold, aluminum, aluminum nitride, aluminum oxide, brass, cobalt, graphite, or beryllium, or any other suitable metal or material. In one embodiment, the one or more pillars are composed of copper. In another embodiment, the pillars are composed of the same material that forms the scaffold support structure. In some embodiments, the pillars are composed of any material capable of forming a desired pillar structure, which is subsequently coated with a metal layer. The metal layer can be applied at an appropriate thickness to allow for suitable pillar conductivity.

In suitable embodiments, the one or more pillars have a width that is appropriate for sufficiently supporting a cell or tissue-embedded hydrogel complex. In one embodiment, the width of the one or more pillars is from about 0.0001-900, 0.001-500, 0.01-50, 0.05-10, or 0.5-5 mm. In another embodiment, the width of the one or more pillars is from about 0.01-50, 0.05-10, or 0.5-5 mm. In a suitable embodiment, the width of the pillars is from about 0.5-5 mm. In other embodiments, the one or more pillars have a diameter that is appropriate for sufficiently supporting a cell or tissue-embedded hydrogel complex. In one embodiment, the diameter of the one or more pillars is from about 0.0001-900, 0.001-500, 0.01-50, 0.05-10, or 0.5-5 mm. In another embodiment, the diameter of the one or more pillars is from about 0.01-50, 0.05-10, or 0.5-5 mm. In a suitable embodiment, the diameter of the pillars is from about 0.5-5 mm.

The positioning and shape of the pillars are also advantageous features of the present disclosure. The morphology and durability of a hydrogel and/or tissue construct will vary depending upon how the pillars are structured and/or disposed on the scaffold. Various configurations can be selected and will be readily apparent to the skilled artisan for specific or desired uses. In one embodiment, the pillars are positioned in angled, straight, slanted, tapered, polygonal, rectangular, square, circular, curved, diagonal, random, concentric, patterned, perimetric, polygonal, diamond, hexagonal, or triangular configurations, or any combination thereof. In some embodiments, the pillars may be disposed on the scaffold surface in a hexagonal pattern to facilitate the growth and stability of various tissue types.

In some embodiments, the shape of the pillars facilitate the adherence and release of cell-hydrogel matrices. The conformation of the pillars may include, but are not limited to, angled, straight, slanted, tapered, round, polygonal, rectangular, square, circular, curved, diagonal, random, concentric, patterned, perimetric, polygonal, or triangular confirmations, or any combination thereof.

The one or more pillars can also be of any length appropriate for sufficiently supporting a cell or tissue-embedded hydrogel complex. In one embodiment, the length of the one or more pillars is from about 0.0001-900, 0.001-500, 0.01-50, 0.05-10, or 0.5-5 mm to about 0.0001-900, 0.001-500, 0.01-50, 0.05-10, or 0.5-5 cm or decimeters (dm). In another embodiment, the length of the one or more pillars is from about 0.01-50, 0.05-10, or 0.5-5 cm or dm. In a suitable embodiment, the length of the one or more pillars is from about 0.5-10 cm or dm. The length of the one or more pillars may also be described in relation to the thickness of the tissue-embedded hydrogel complex. In this regard, length of the one or more pillars is from about 1-100, 5-90, 10-80, 20-70, 30-60, or 40-50% of the thickness of the hydrogel complex.

In one aspect, the present disclosure provides for a thermoresponsive polymer that is configured to coat the thermoconductive scaffold and one or more pillars, wherein the polymer is able to transition from a hydrophobic state to a hydrophilic state in response to a change in temperature. Such hydrodynamic transitions may occur at suitable temperatures or temperature ranges. In one embodiment, the transition occurs at a temperature from about 1-100, 5-80, 10-70, 15-60, 20-50, 25-40, 30-35° C., or at about 32° C. In suitable embodiments, the hydrodynamic transition occurs at about 32° C.

Such hydrodynamic fluctuations permit cell attachment and release as a function of heat and polymer thickness. This phenomenon can be correlated with an adsorption of cell adhesion proteins, e.g., fibronectin, onto surfaces coated in an appropriate polymer. In suitable embodiments, the thermoresponsive polymer is poly(N-isopropylacrylamide) (PIPAAm), isopropylacrylamide butyl methacrylate copolymer (IBc), butyl methacrylate (BMA), poly-NIPAAm-co-AAc-co-tBAAm (IAtB), N,N-dimethylaminopropylacrylamide (DMAPAAm), poly(N-acryloylpiperidine)-cysteamine (pAP), PIPAAM-carboxymethyl dextran benzylamide sulfonate/sulfate (PIPAAm-CMDBS), or N,N-methylene-bis-acrylamide cross-linked polymer, or any combinations thereof. In an illustrative embodiment, the thermoresponsive polymer is PIPAAm.

PIPAAm is a suitable amphipathic polymer in that it can change its polarity for water in response to a change in temperature. See, e.g., Akiyama et al., *Ultrathin poly(N-isopropylacrylamide) grafted layer on polystyrene surfaces for cell adhesion/detachment control*. Langmuir. Vol. 21(13), pp. 5506-5511 (2004). Accordingly, at appropriate temperatures, the hydrogel matrix is mechanically supported by the substrate and associated pillars coated in a thermoresponsive polymer, which permits cell attachment and proliferation.

The thermoresponsive polymer, e.g., PIPAAm, can be applied as a thin film by various applications known in the art, such as grafting, spraying, binding, interacting, mixing, brushing, layering, and the like. In suitable embodiments, the thermoresponsive polymer is grafted onto the thermoconductive substrate. In one embodiment, PIPAAm is grafted onto a copper scaffold containing one or more copper pillars. For example, a copper scaffold is obtained and washed with hydrochloric acid to remove any oxide, rinsed with deionized water and isopropyl alcohol (IPA), and dried. Subsequently, a 1% polystyrene-toluene solution (v/v) is sprayed on the copper support at a temperature of 80° C., thereby coating the scaffold.

In order to create polymer initiation sites, the coated copper pillars are placed in a chamber and treated with an argon plasma for 5 min at <0.1 mm Hg. The chamber is then flooded with dry nitrogen. Subsequently, degassed n-isopropylacrylamide in IPA (10 g/L) is introduced into the chamber for 1 hour. When the grafting is complete, the pillars are removed from the chamber, rinsed with IPA, and dried.

Cell surface adhesion to a thermoresponsive polymer is influenced by the polymer's thickness because the polymer substrate influences the hydrophobicity of the system, and thus, the adherent nature of the scaffold-tissue complex. In one embodiment, the thickness and graft density of the thermoresponsive polymer may be adjusted so that the hydrophobic surface of the base layer, e.g., polystyrene, is accessible to cells while the thermoresponsive coating is also hydrophobically adherent. Moreover, in one embodiment, the polymer's thickness effectively shields the cells from the polystyrene in the non-adherent, hydrophilic state. As such, the transition from adherent to non-adherent states is readily achievable.

The thickness of the thermoresponsive polymer layer can be from about 0.001-100, 0.01-10, or 0.1-1 picometers (pm) to from about 0.001-900, 0.01-100, 0.1-70, 1-50, or 15-30 nm. In one embodiment, the thickness of the thermoresponsive polymer layer is from about 0.001-900, 0.01-100, 0.1-70, 1-50, or 15-30 nm. In suitable embodiments, the thickness of the thermoresponsive polymer layer is from about 15-30 nm. Likewise, the thickness of the PIPAAm layer can be from about 0.001-100, 0.01-10, or 0.1-1 picometers (pm) to from about 0.001-900, 0.01-100, 0.1-70, 1-50, or 15-30 nm. In one embodiment, the thickness of the PIPAAm layer is from about 0.001-900, 0.01-100, 0.1-70, 1-50, or 15-30 nm. In suitable embodiments, the thickness of the PIPAAm layer is from about 15-30 nm.

Methods for Hydrogel Production and Tissue Engineering

In one aspect, the present disclosure provides methods for tissue engineering, which include applying a hydrogel solution to a thermoconductive scaffold, with one or more pillars, coated in a thermoresponsive polymer, and allowing the hydrogel solution to congeal. In this regard, the hydrogel solution can be any solution suitable for the purpose of producing a hydrogel as described herein. In some embodiments, the hydrogel solution may include, but is not limited to, poly(hyaluronic acid), poly(sodium alginate), poly(ethylene glycol), diacrylate, and/or chitosan, or any combination thereof.

Hydrogels are typically manufactured from liquid components that require time to solidify or congeal. In general, hydrogels can congeal in minutes, hours, days, or weeks. In one embodiment, the hydrogel is allowed to congeal for about 0.5, 1, 2, 3, 4, 5, 6, 7, 8, 9, 10, 20, 30, or 50 hours (h). In another embodiment, the hydrogel is allowed to congeal for about 5, 6, or 7 h. It will be readily apparent to the skilled artisan that numerous additional variables can effect hydrogel polymerization, solidification, or congealing. These factors such as, for example, humidity, $CO_2$ concentration, and/or temperature, etc., are contemplated, such that appropriate adjustments can optimize cell and tissue production.

Once the hydrogel has congealed, and the cells contained within the hydrogel are ready for harvesting, e.g., patient implantation or other final use, the polymer-coated thermoconductive substrate, with attached pillars, can be cooled to allow for tissue-scaffold separation. In suitable embodiments, the temperature decrease is below the critical temperature of the thermoresponsive polymer, i.e., a temperature capable of hydrodynamically altering the polarity of the polymer. Such thermoresponsive transformations facilitate a change from a hydrophobic to a hydrophilic state of the polymer, thereby releasing the attached cells or tissues without disruption of the ECM.

Along these lines, the polymer can be any thermoresponsive polymer capable of transitioning from a hydrophobic state to a hydrophilic state or, conversely, from a hydrophilic state to a hydrophobic state in response to a change in temperature, as described above.

Thus, by decreasing the temperature of the thermoconductive scaffold, an associated decrease in temperature of the thermoresponsive polymer facilitates the release of the hydrogel, i.e., from the scaffold and pillars. To this point, thermoresponsive PIPAAm transitions from a hydrophobic coiled state to a hydrophilic gel state at or below 32° C. In this regard, thin films composed of PIPAAm are not only advantageous for facilitating cellular release as part of cell-sheet tissue engineering, but also for assisting the development of larger tissue constructs prone to cracking or disintegration. The one or more thermoconductive pillars, attached to a metal supporting scaffold, e.g., copper, are cooled to the PIPAAm critical transition state temperature of 32° C., or below, thereby facilitating the PIPAAm hydrophilic transition. This phase transition no longer supports a cell-adhesive surface for the hydrogel-tissue complex, and, in turn, the cells and/or tissue are released in an intact, non-disruptive manner. The temperature-induced hydrophilic/hydrophobic properties of PIPAAm can also be affected by the amount, i.e., thickness, of its application, which in turn affects cell adhesion and/or detachment.

Cooling of the thermoconductive scaffold, including the one or more pillars, facilitates the release of the tissue matrix complex from the thermoconductive scaffold as described above. The skilled artisan will readily appreciate that various methods known in the art can be employed for cooling the thermoconductive scaffold, e.g., thermoelectric cooling devices. One such illustrative method is by implementing a Peltier cooler or device. Peltier devices are portable and appropriate for cooling small instruments and electronic components. Typically, Peltier coolers include thermal cylinders, which can be used for DNA synthesis via PCR (polymerase chain reaction). These devices can readily be adapted for use in the methods described herein.

Maintaining an appropriate tissue temperature, and/or hydrogel-tissue complex temperature, is also a facet of cell and tissue engineering. If proliferating cells or tissues are cooled too quickly or to a degree below biological viability, the resulting tissue could be rendered inert. Accordingly, the thermoconductive pillars are capable of rapid cooling, thereby allowing the pillar/hydrogel PIPAAm interface to cool without compromising the temperature of the tissue therewith. Consequently, the hydrogel-tissue complex can be removed from the scaffold-pillar support, while maintaining the viability and structure of the cells and/or tissue.

As described herein, the one or more pillars can be of various widths and/or lengths to provide for suitable tissue related adaptations, prior to or during tissue construction. It will be readily apparent to the skilled artisan that larger hydrogel-tissue structures require robust, i.e., thicker and taller, pillars compared to smaller applications thereof. The methods of the present disclosure further envisage pillars of different conformations and/or configurations on the support structure. In one embodiment, the one or more pillars are positioned throughout the thermoconductive scaffold in angled, straight, slanted, tapered, polygonal, rectangular, square, circular, curved, diagonal, random, concentric, patterned, perimetric, polygonal, or triangular configurations, or any combination thereof. Moreover, the methods described herein contemplate detachable or fixed pillar structures, each adaptable for use and implementation as required for various hydrogel or tissue engineering applications. In one embodiment, the pillars do not extend beyond the surface of the hydrogel matrix. In another embodiment, the pillars are configured to traverse the surface of the hydrogel matrix.

Subsequent to release, the hydrogel-tissue complex may contain micrometer to millimeter sized holes, cavities, permutations, or indentations, that are proportionate to the amount and size of the one or more pillars. These voids left in the hydrogel can be filled with additional hydrogel solution at any time. The hydrogel can also "heal" itself by allowing cells and/or tissue proliferation to act as biological fillers or plugs, which grow into the perforations, indentations, holes and/or cavities.

The hydrogel matrices are capable of facilitating tissue growth, tissue engineering, cell growth, and/or cell-sheet growth. However, cellular proliferation depends upon numerous factors including, but not limited to, the type of cell culture, the frequency of sub-culturing, the type of media employed and how often it is replenished, and the length of time the cells are cultured, etc.

Cell culturing may be performed and modified, as desired, for suitable cell density and/or confluence, which can be for about 1, 2, 3, 4, 5, 6, 7, 8, 9, 10, 11, 12, 13, 14, 15, 16, 17, 18, 19, 20, 25, 30, 35, 40, or 50 days. In some embodiments, the cells are cultured for about 13, 14, 15, 16, 17, or 18 days. In one embodiment, the cells are cultured until a desired cell density is attained. In one embodiment, the cells are cultured until they are grown to confluence. The amount of time required for cell culturing may depend upon the type of cell cultured. Cell culture media, e.g., DMEM, can be replenished as required for suitable cell and tissue growth.

Tissue engineering includes producing tissues that emanate from one or more various cell-types. As such, it is contemplated that different cell-types can be employed for the methods disclosed herein, which include, but are not limited to, human or mammal skin cells, muscle cells, epithelial cells, endothelia cells, stem cells, umbilical vessel cells, corneal cells, cardiomyocytes, aortic cells, corneal epithelial cells, aortic endothelial cells, fibroblasts, hair cells, keratinocytes, melanocytes, adipose cells, bone cells, osteoblasts, airway cells, microvascular cells, mammary cells, vascular cells, chondrocytes, and/or placental cells. In one embodiment, fibroblasts are employed for tissue and/or organ generation. In another embodiment, keratinocytes are employed for tissue and/or generation.

Furthermore, in addition to various cell-types, a variety of cell or tissue applications can be implemented in accord with the present methods. These applications include, but are not limited to, producing cell-layers that are suitable for cell and tissue grafting, skin-grafting, allografting, wound healing grafts, skin replacement, ocular reconstruction, liver tissue reconstruction, cardiac patching, or bladder augmentation, or any combination thereof.

Additionally, one or more cell-layers, cells, tissues, and/or other biological outgrowths can be produced from the methods disclosed herein, and include, but are not limited to, monolayers, stratified layers, spheroid cell-bodies, tubular cell-bodies, hollow cell-bodies, graded porosity masses, and/or solid masses, or any combination thereof. These methods are suitable for cell and tissue engineering, as well as cell immobilized applications relating thereto.

Tissue engineering is enhanced by the support complexes of the present disclosure in that they allow for cell and tissue growth, such that the products produced therefrom can be harvested in a non-invasive manner. In this regard, the cells, tissues, and/or other biological products are harvested prior to use. Harvesting tissues may include separation of the hydrogel matrix from cells or tissues. Various methods for separating natural or synthetic hydrogel matrices from the cells or tissues are known in the art and may include proteolytic cleavage, competitive binding, and/or molecular degradation of the hydrogel, etc.

FIG. 1 shows an illustrative embodiment of the apparatus 100 that may be used in accordance with the present methods. In an apparatus 100, cell proliferation is facilitated by employing a thermoconductive scaffold 110. The thermoconductive scaffold 110 contains one or more thermoresponsive pillars 120 projecting outward. In an apparatus 100, a thermoresponsive polymer 130 is applied to the thermoconductive scaffold 110 and the one or more pillars 120. The thermoresponsive polymer 130, such as PIPAAm, typically has a critical phase transition temperature of about 32° C. In an apparatus 100, the one or more pillars 120, coated in a thermoresponsive polymer 130, penetrate a hydrogel matrix 140 congealed thereon, at multiple places. The hydrogel matrix 140 is suitable for cell proliferation and/or tissue construction.

In an apparatus 100, the cells are grown to a desired density and/or form a desired tissue construct on the hydrogel matrix 140. Subsequently, in an apparatus 100, the thermoconductive scaffold 110 is cooled by a Peltier cooler 150. Upon cooling, and attendant thermoresponsive polymer 130 hydrophilic transition, the tissue releases from the one or more pillars 120, thereby, leaving holes that can be filled with additional hydrogel matrix 140. The holes can also be allowed to heal naturally through the process of cell proliferation in bioreactor media or as an implant inside a patient.

Kits for Hydrogel Production and Tissue Engineering

One aspect of the present technology discloses a kit containing reagents and instructions for performing the present methods. The kit includes a support for tissue engineering composed of a thermoconductive scaffold with one or more pillars. The thermoconductive scaffold and pillars may be made of copper, silver, zinc, magnesium, iron, gold, aluminum, aluminum nitride, aluminum oxide, brass, cobalt, graphite, and beryllium, or any combination thereof. The kit may further include a thermoresponsive polymer coating the one or more pillars, wherein the thermoresponsive polymer is capable of transitioning from a hydrophobic to a hydrophilic state in response to a change in temperature.

In one embodiment, the kit includes PIPAAm as a thermoresponsive polymer. In accord with the methods described herein, the kit may include a hydrogel solution, wherein the hydrogel matrix is capable of facilitating cell growth, tissue growth, cell-layer or cell-sheet growth, monolayer or stratified layer cell growth, tissue growth, organ production, and/or tissue engineering, or any combination thereof. The hydrogel solution contained within the kit can include poly(hyaluronic acid), poly(sodium alginate), poly(ethylene glycol), diacrylate, or chitosan, or any combination thereof. The kit may also include a Peltier cooler. In one embodiment, the kit discloses reagents and instructions for performing or producing any of the methods, steps, procedures or embodiments described herein.

EXAMPLES

The present compositions and methods will be understood more readily by reference to the following examples, which are provided by way of illustration and are not intended to be limiting in any way.

Example 1

Fabrication of a Thermoconductive Scaffold with Thermoresponsive Polymer

A tissue engineering scaffold is manufactured from a copper substrate. Pillar apertures are positioned throughout the base of the scaffold in a hexagonal pattern. In this regard, the apertures may be pre-formed with the copper substrate or drilled into a copper scaffold. Subsequently, 0.5 mm×2.0 cm copper pillars (diameter×height) are reversibly affixed to the scaffold by inserting the pillars into the apertures, thereby creating the scaffold-pillar foundation. The scaffold, with attached pillars, is then washed with HCl and rinsed in deionized water. Isopropyl alcohol (IPA) is then applied to the scaffold, which is allowed to dry at room temperature. Next, a 1% polystyrene-toluene solution (v/v) is sprayed onto the scaffold and pillars at 80° C. A suitable thermoresponsive polymer from Table 1 is then covalently grafted onto the scaffold-pillar surface to a thickness of 15 nm via electron beam irradiation using argon plasma for 5 min at <0.1 mm Hg. The irradiation chamber is flooded with dry nitrogen, and degassed n-isopropylacrylamide in IPA (10 g/L) is introduced for 60 min. The scaffold is then removed from the chamber, rinsed with IPA, and placed on a Peltier cooler for subsequent tissue engineering applications.

TABLE 1

Scaffold Applications

| THERMORESPONSIVE POLYMERS | THERMOCONDUCTIVE MATERIALS |
|---|---|
| Poly(N-isopropylacrylamide) (PIPAAm), isopropylacrylamide butyl methacrylate copolymer (IBc), butyl methacrylate (BMA), poly-NIPAAm-co-AAc-co-tBAAm (IAtB), N,N-dimethylaminopropylacrylamide (DMAPAAm), poly(N-acryloylpiperidine)-cysteamine (pAP), PIPAAM-carboxymethyl dextran benzylamide sulfonate/sulfate (PIPAAm-CMDBS), or N,N-methylene-bis-acrylamide cross-linked polymer. | Copper, silver, zinc, magnesium, iron, gold, aluminum, aluminum nitride, aluminum oxide, brass, cobalt, graphite, or beryllium. |

Example 2

Tissue Engineering

A thermoconductive scaffold is produced by layering a suitable thermoconductive material from Table 1 on a plastic substrate containing orthogonally positioned pillars. PIPAAm is subsequently grafted onto the thermoconductive scaffold to a thickness of 15 nm, as described above. Under sterile conditions, tissue specific cells are cultured with a hydrogel matrix solution selected from Table 2 and applied to the scaffold, as described below. Briefly, $5 \times 10^4$ cells/mL in 1 mL of Dulbecco's Modified Eagle's Medium (DMEM) are incubated with the hydrogel solution for 30 min at 37° C. or until a suitable hydrogel and cell density are formed. The cell-hydrogel solution is applied to the scaffold and the cells are allowed to proliferate. The cell-hydrogel solution may be sustained at 37° C. with 5% CO$_2$ for several days After the hydrogel has congealed and an appropriate tissue construct has developed, the thermoconductive scaffold with grafted PIPAAm, and concomitant hydrogel-tissue construct, is placed on a Peltier cooler and cooled to 32° C. The thermally conductive pillars are rapidly cooled, thereby initiating the hydrophobic to hydrophilic phase change at the PIPAAm interface without altering tissue temperature of the entire construct. As such, the newly formed hydrogel-tissue complex no longer adheres to the hydrophilic scaffold. Accordingly, the hydrogel-tissue complex can be separated from the scaffold in a non-disruptive manner thus ensuring the integrity of the tissue construct.

TABLE 2

Hydrogel Solutions
HYDROGEL MATRICES

Polyglycolic acid; Polylactic acid; Polylactide-glycolide; Polydioxanone; Poly(hyaluronic acid); Poly(sodium alginate); Poly(ethylene glycol); Poly(lactic acid); Poly(glycolic acid); Poly(lactide-co-glycolides); Poly(urethanes); Poly(siloxanes); Poly(ethylene); Poly(vinyl pyrrolidone); Poly(2-hydroxy ethyl methacrylate); Poly(N-vinyl pyrrolidone); Poly(methyl methacrylate); Poly(vinyl alcohol); Poly(acrylic acid); Poly(vinyl acetate); polyacrylamide; Poly(ethylene-co-vinyl acetate); Poly(methacrylic acid); Nylons; Polyamides; Polyanhydrides; Poly(ethylene-co-vinyl alcohol); Polycaprolactone; Polyvinylhydroxide; Poly(ethylene oxide); Diacrylate; or Chitosan.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 proteins refers to groups having 1, 2, or 3 proteins. Similarly, a group having 1-5 proteins refers to groups having 1, 2, 3, 4, or 5 proteins, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

The invention claimed is:

1. A support for tissue engineering comprising:
   a thermoconductive scaffold with one or more pillars, wherein the one or more pillars have a length from about 0.5 cm to 10 cm and a diameter from about 0.5 mm-5 mm; and
   a thermoresponsive polymer coating the one or more pillars, wherein the thermoresponsive polymer is capable of transitioning from a hydrophobic to a hydrophilic state in response to a change in temperature.

2. The support of claim 1, wherein the thermoconductive scaffold is made of a material selected from the group consisting of copper, silver, zinc, magnesium, iron, gold, aluminum, aluminum nitride, aluminum oxide, brass, cobalt, graphite, and beryllium, or any combination thereof.

3. The support of claim 1, wherein the thermoconductive scaffold is made of copper.

4. The support of claim 1, wherein the one or more pillars are positioned throughout the thermoconductive scaffold in angled, straight, slanted, tapered, polygonal, rectangular, square, circular, curved, diagonal, random, concentric, patterned, perimetric, polygonal, diamond, hexagonal, or triangular configurations, or any combination thereof.

5. The support of claim 1, wherein the thermoresponsive polymer is PIPAAm.

6. The support of claim 5, wherein the PIPAAm is hydrophobic at temperatures above 32° C. and wherein the PIPAAm is hydrophilic at 32° C. or below.

7. A kit for providing tissue engineering support comprising:
   a thermoconductive scaffold with one or more pillars, wherein the one or more pillars are coated in a thermoresponsive polymer, and wherein the length of the one or more pillars is from about 0.5 cm to 10 cm and the diameter is from about 0.5 mm-5 mm;
   one or more hydrogel components; and
   instructions for making the support.

* * * * *

UNITED STATES PATENT AND TRADEMARK OFFICE
CERTIFICATE OF CORRECTION

PATENT NO. : 8,790,926 B2
APPLICATION NO. : 13/260021
DATED : July 29, 2014
INVENTOR(S) : Miller Page 1 of 1

It is certified that error appears in the above-identified patent and that said Letters Patent is hereby corrected as shown below:

In the Specification:

In Column 3, Line 60, delete "poly(-hydroxy" and insert -- poly(2-hydroxy --, therefor.

In Column 7, Line 54, delete "Vol. 21(13)," and insert -- Vol. 20(13), --, therefor.

Signed and Sealed this
Twenty-fifth Day of November, 2014

Michelle K. Lee
*Deputy Director of the United States Patent and Trademark Office*